United States Patent [19]

Fielden

[11] Patent Number: 5,556,639
[45] Date of Patent: Sep. 17, 1996

[54] WATER-DISPERSIBLE TABLETS

[75] Inventor: Krystyna E. Fielden, Dartford, United Kingdom

[73] Assignee: Glaxo Wellcome Inc., Research Triangle Park, N.C.

[21] Appl. No.: 90,111

[22] PCT Filed: Jan. 29, 1992

[86] PCT No.: PCT/GB92/00163

§ 371 Date: Jul. 13, 1993

§ 102(e) Date: Jul. 13, 1993

[87] PCT Pub. No.: WO92/13527

PCT Pub. Date: Aug. 20, 1992

[30] Foreign Application Priority Data

| Jan. 31, 1991 | [GB] | United Kingdom | 9102019 |
| Nov. 22, 1991 | [GB] | United Kingdom | 9124803 |
| Nov. 22, 1991 | [GB] | United Kingdom | 9124807 |
| Nov. 25, 1991 | [GB] | United Kingdom | 9125005 |

[51] Int. Cl.$^6$ ................................. A61K 9/34
[52] U.S. Cl. ............ 424/480; 424/464; 424/465
[58] Field of Search ................ 427/3; 424/464, 424/465, 480

[56] References Cited

U.S. PATENT DOCUMENTS

| 3,427,379 | 2/1969 | Barry et al. | 514/161 |
| 3,432,593 | 3/1969 | Shepard | 514/158 |
| 3,567,819 | 3/1971 | Leonia et al. | 514/557 |
| 4,072,535 | 2/1978 | Short et al. | 106/210 |
| 4,086,335 | 4/1978 | Bruscato et al. | 514/161 |
| 4,159,345 | 6/1979 | Takeo et al. | 514/781 |
| 4,209,513 | 6/1980 | Torode et al. | 514/158 |
| 4,251,518 | 2/1981 | Moore et al. | 514/54 |
| 4,304,773 | 12/1981 | Wong et al. | 514/223.2 |
| 4,305,502 | 12/1981 | Gregory et al. | 206/532 |
| 4,322,449 | 3/1982 | Voss et al. | 427/2.14 |
| 4,369,308 | 1/1983 | Trubiano | 536/106 |
| 4,371,516 | 2/1983 | Gregory et al. | 424/485 |
| 4,414,198 | 11/1983 | Michaelson | 424/44 |
| 4,517,179 | 5/1985 | Raghunathan | 514/249 |
| 4,600,579 | 7/1986 | Salpekar et al. | 514/629 |
| 4,602,017 | 7/1986 | Sawyer et al. | 514/242 |
| 4,631,305 | 12/1986 | Guyer et al. | 523/400 |
| 4,661,521 | 4/1987 | Salpekar et al. | 514/613 |
| 4,711,777 | 12/1987 | Tan et al. | 514/158 |
| 4,757,090 | 7/1988 | Salpekar et al. | 514/613 |
| 4,774,083 | 9/1988 | Tan et al. | 424/78.11 |
| 4,781,925 | 11/1988 | Michelucci et al. | 424/465 |
| 4,832,956 | 5/1989 | Gergely et al. | 424/466 |
| 4,837,031 | 6/1989 | Denton | 424/464 |
| 4,847,249 | 7/1989 | Sawyer et al. | 514/242 |
| 4,904,477 | 2/1990 | Ho et al. | 424/465 |
| 4,910,023 | 3/1990 | Botzolakis et al. | 424/470 |
| 4,925,676 | 5/1990 | Sellassie et al. | 424/470 |
| 4,927,639 | 5/1990 | Sellassie et al. | 424/497 |
| 4,950,484 | 8/1990 | Olthoff et al. | 424/464 |
| 4,965,072 | 10/1990 | Alexander et al. | 424/458 |
| 4,968,517 | 11/1990 | Gergely et al. | 426/285 |
| 4,970,078 | 11/1990 | Holinej | 424/465 |
| 4,999,200 | 3/1991 | Casillan | 424/480 |
| 5,006,345 | 4/1991 | Lang | 424/467 |
| 5,037,658 | 8/1991 | Urban et al. | 424/469 |
| 5,047,247 | 9/1991 | Milovac et al. | 424/465 |
| 5,049,586 | 9/1991 | Ortega et al. | 514/557 |
| 5,064,656 | 11/1991 | Gergely et al. | 424/463 |
| 5,069,910 | 12/1991 | Kovacic et al. | 424/464 |
| 5,073,377 | 12/1991 | Alexander et al. | 424/458 |
| 5,085,869 | 2/1992 | Olthoff et al. | 424/464 |
| 5,087,454 | 2/1992 | Duerholz et al. | 424/464 |
| 5,136,080 | 8/1992 | Miller et al. | 558/410 |

FOREIGN PATENT DOCUMENTS

| 53042/90 | 2/1990 | Australia . |
| 0261595B1 | 3/1988 | European Pat. Off. . |
| 0294933 | 5/1988 | European Pat. Off. . |
| 0305843A2 | 3/1989 | European Pat. Off. . |
| 0350701A2 | 1/1990 | European Pat. Off. . |
| 0391851A1 | 3/1990 | European Pat. Off. . |
| 0372934A2 | 6/1990 | European Pat. Off. . |
| 0459819 | 12/1991 | European Pat. Off. . |
| 0459830A1 | 12/1991 | European Pat. Off. . |
| 0265226 | 5/1992 | European Pat. Off. . |
| 2016622 | 10/1971 | Germany . |
| 43-24078 | 10/1968 | Japan . |
| 777516 | 6/1957 | United Kingdom . |
| 837451 | 6/1960 | United Kingdom . |
| 1317400 | 5/1973 | United Kingdom . |
| 1421964 | 1/1976 | United Kingdom . |
| 1443023 | 7/1976 | United Kingdom . |
| 1480188 | 7/1977 | United Kingdom . |
| 1480175 | 7/1977 | United Kingdom . |
| 1533243 | 11/1978 | United Kingdom . |
| 1546448 | 5/1979 | United Kingdom . |
| 1548022 | 7/1979 | United Kingdom . |
| 2033225 | 5/1980 | United Kingdom . |
| 1601833 | 11/1981 | United Kingdom . |
| 2086725 | 5/1982 | United Kingdom . |
| 2124078 | 2/1984 | United Kingdom . |
| 2157170 | 10/1985 | United Kingdom . |
| 2249957 | 5/1992 | United Kingdom . |
| 83/00809 | 3/1983 | WIPO . |
| 87/05804 | 10/1987 | WIPO . |
| 91/03241 | 3/1991 | WIPO . |
| 91/07174 | 5/1991 | WIPO . |
| WO92/09270 | 6/1992 | WIPO . |

OTHER PUBLICATIONS

Thirty–seven Patent Abstracts from World Patents Index (1967–1990) related to Magnesium Aluminum Silicate.

(List continued on next page.)

*Primary Examiner*—Jyothsna Venkat
*Attorney, Agent, or Firm*—Donald Brown; George W. Neuner

[57] ABSTRACT

A water-dispersible tablet comprises lamotrigine, a pharmaceutically acceptable swellable clay and an additional disintegrating agent. The swellable clay and an additional disintegrating agent. The swellable clay is a smectite, e.g. Veegum F or bentonite, and is present within the granules of the tablet to provide a tablet which is capable of dispersing in water within 3 minutes to provide a dispersion which will pass through a 710 μm sieve. The tablet can be optionally film-coated in which case the dispersion time is less than 5 minutes.

9 Claims, No Drawings

OTHER PUBLICATIONS

Thirty-six abstracts from chemical Abstracts (1967–present) related to Dispersible Tablet Formulations Based on Veegum–type Magnesium Aluminum Silicate.

Veegum—The Natural Ingredient: R. T. Vanderbilt & Co., p. 9.

Veegum—The Supernatural Ingredient: R. T. Vanderbilt & Co., Booklet (1987).

Veegum—The Versatile Ingredient for Pharmaceutical Formulations: R. T. Vanderbilt & Co., Booklet.

Pharmasorb: Lawrence Industries. pp. 1–10 (1986).

Polargel White Bentonite: American Colloid Co., Booklet.

Mastery in Refinement—Magnabrite & Polargel: American Colloid Co.

Wai, et al., "Applications of the Montmorillonites in Tablet Making," J. Pharm. Sci., 55: 1244–1248 (1966).

Wai & Banker, "Some Physicochemical Properties of the Montmorillonites," J. Pharm. Sci., 55: 1215–1220 (1966).

Granberg, et al., "The Use of the Dried Bentonite as a Disintegrating Agent in Compressed Tablets of Thyroid," J. Am. Pharm. Assoc. Sci., 43: 648–651 (1949).

Gross, et al., "A Comparative Study of Tablet Disintegrating Agents," J. Am. Pharm. Assoc. Sci., 41: 157–161 (1952).

Firouzabadian, et al., "Some Recently Developed Chemicals as Disintegrating Agents for Compressed Tablets," J. Am. Pharm. Assoc. Sci., 43: 248–250 (1954).

Ward, et al., "Evaluation of Tablet Disintegrants," Drug Cosmetic Ind. 91: 35–36, 92, 110–111 (1962).

Nair, et al., "Studies on Disintegration of Compressed Tablets I. Effect on Disintegration of the Procedure Used in Incorporating the Disintegrating Agent," J. Am. Pharm. Assoc. Sci., 46: 131–134 (1957).

Patel, et al., "Veegum as Binding Agent for Compressed Tablets," Indian J. Pharm., 19: 4–10 (1957).

Feinstein, et al., "Comparative Study of Selected Disintegrating Agents," J. Pharm. Sci. 55: 332–334 (1966).

Varley, A., "The Generic Inequivalence of Drugs," JAMA, 206: 1745–1748 (1968).

Delonca, et al., "Study of the Activity of Some Disintegrants as a Function of Procedure and of the Solubility of the Active Principles," J. Pharm. Belg. 26(4): 447–458 (1971)—English Translation.

Wagner, et al., "In Vivo and In Vitro Availability of Commerical Warfarin Tablets," J. Pharm. Sci. 60: 666–677 (1971).

McGinty, et al., "Optimization of Slow–Release Tablet Formulations Containing Montmorillonite I. Properties of Tablets," Drug Development and Industrial Pharmacy 6: 399–410 (1980).

Bargava, et al., "An Evaluation of Smecta as a Tablet Disintegrant and Dissolution Aid," Drug Development and Industrial Pharmacy 17: 2093–2102 (1991).

Barr, M., "In Pharmaceutical Systems . . . Clays as Dispersion Stabilizers," J. Amer. Pharm. Assoc. Sci. Ed. 46: 486–493 (1957).

US Pharmacopoeia, pp. 579, 1573, 1574, 1534 and 1535 (1985).

British Pharmacopoeia, pp. 27, 28, 51, 52, 62, 323–325 (1985).

Martindale, The Extra Pharmacopoeia, 29th Edition, pp. 4, 1077, 1092 and 1433.

The Handbook of Pharmaceutical Excipients, pp. 9–11, 150–152, 166–169.

Armstrong, N., "Tableting" from Pharmaceutics: The Science of Dosage Form Design, (Ed. Aulton): 647–668 (1988).

Rubinstein, M., "Tablets" from Pharmaceutics: The Science of Dosage Form Design, (Ed. Aulton): 304–321 (1988).

Rudnic, et al., "Oral Solid Dosage Forms," from Remington's Pharmaceutical Sciences (ed. Gennaro), pp. 1633–1665 (1990).

Disanto, A., "Bioavailability and Bioequivalency Testing," from Remington's Pharmaceutical Sciences (ed. Gennaro), pp. 1451–1458 (1990).

Banker, et al., "Tablets," from The Theory and Practice of Industrial Pharmacy, pp. 293–345.

Marshall, et al., "Tablet Dosage Forms," from Modern Pharmaceutics (eds., Banker, G. & Rhodes, C.) pp. 355–425 (1990).

Shangraw, R., "Specialty Tablet and Capsules," from Modern Pharmaceutics (eds. Banker, G. & Rhodes, C.) pp. 427–440 (1990).

British Pharmacopoeia 1988, vol. II; pp. 891–895.

Derwent equivalent search report.

International search report PCT/GB93/01586.

Japan abstract kokai No. 1–93541; (1987).

Hagers's Handbook of Pharmaceutical Practice, 4th Edition, vol. 7; part B pp. 271–281.

Faracja Polska (1966); No. 7; pp. 505–509.

Acta Poloniae Pharmaceutica; 15; No. 4, 1968; four pages.

WATER-DISPERSIBLE TABLETS

The present invention relates to a water-dispersible tablet formulation containing a therapeutically active compound.

Therapeutically active compounds or drugs are frequently administered to patients in tablet form where the drug is intended for oral administration since tablets are an especially convenient pharmaceutical form for manufacture, storage and generally usage. However, problems, may arise with the administration of such tablets to patients who have difficulty in swallowing the tablets (for example, children or more seriously ill patients) especially if the tablets are large in size arising from the amount of drug required in each tablet. A solution to such problems is to formulate the tablets in a form whereby they can be dispersed in water to form a dispersion containing the drug which can then be drunk by the patient.

Known water-dispersible tablets include effervescent formulations which rely on the formation of a gas to quickly break up the tablet, but these involve expensive methods of manufacture and strict regulations for such manufacture. Other known water-dispersible tablets use disintegrating agents such as microcrystalline cellulose used in Feldene® R dispersible tablets. We have tested well-known disintegrating agents (incorporated both internally and externally to the preformed granules) such as sodium starch glycollate (e.g. Explotab), cross-linked povidone (e.g. Kollidon CL) and a cross-linked sodium carboxymethylcellulose (e.g. Ac-Di-Sol) in an acyclovir tablet, but found that they did not provide a satisfactory water-dispersible formulation. We furthermore tested an ion exchange resin (Amberlite 1RP88) as a disintegrating agent and incorporated surface active agents (e.g. sodium lauryl sulphate and sodium docusate) in an attempt to improve tablet wetting and penetrating of water during dispersion, but in all cases the disintegration time was high.

After considerable research and investigation, we have now suprisingly found that the use of a swellable clay within the granulate of a lamotrigine tablet formulation provides a tablet which has good dispersibility in water to provide a dispersion which can be drunk by a patient.

Swellable clays such as Veegum$^R$ and other magnesium aluminium silicates have previously been studied and proposed for use as disintegrating agents, binders and lubricants in the manufacture of tablets, but such studies and proposals were exclusively with respect to tablets intended for swallowing and not for water-dispersible tablets (Rubenstein, Pharmaceutics—The Science of Dosage Form Design (1990) for disintegrants see p 312 and 314). Moreover, there has never been any suggestion that a clay would be suitable to meet the more stringent requirements for dispersible tablets. Tablets for swallowing need only have a disintegration time in water of less 15 minutes and be able to form particles on disintegration in water that can pass through a 2.00 mm mesh aperture (British Pharmacopia test for swallowable tablets). Such long disintegration times and large particle sizes are entirely unsuitable for a dispersible tablet.

Even when swellable clays have been proposed as disintegrating agents for swallowable tablets, they are not regarded as very suitable for such use because their off-white appearance can often discolour the tablet and because they are not as effective as other disintegrating agents (Banker and Anderson—Theory and Practice of Industrial Pharmacy p 328 (1986) and Bhargava et al—Drug Development and Industrial Pharmacy, 17(15), 2093-2102(1991)). In fact, bentonire is identified in Marshall and Rudnic, Modern Pharmaceutics (1990) p 374, as the least swellable of the ten disintegrants listed. There is no mention in the above textbook references of how the swellable clay should be incorporated—i.e. by intra-granular addition or by extra-granular addition. In the former case, the clay would be included in the mixture from which the granulate is formed; in the latter case the clay would be added to the pre-formed granulate. In J. Pharm. Sci, 55, 1244 (1966), Wai et al. reviewed the following papers relating to swellable clays such as Veegum and bentonire as disintegrating agents: Wai et al., J. Pharm. Sci, 55, 1215(1966); Granberg et al., J. Am. Pharm. Assoc. Sci, 38, 648(1949); Gross et al., J. Am. Pharm. Assoc. Sci, 41, 157(1952); Firouzabadian et al., J. Am. Pharm. Assoc. Sci, 43,248(1954); Ward et al., Drug Cosmetic Ind, 91, 35(1962); Nair et al., J. Am. Pharm. Assoc. Sci, 46,131(1957); and Patel et al., Indian J. Pharm., 19, Jan.1957. Wai et al., then compared three grades of Veegum evalulating both extra-granular and intra-granular addition and concluded that "the clays were not good disintegrating agents when wet granulated" (i.e. intra-granular addition), and then went on to recommend extra-granular addition. Furthermore R. T. Vanderbilt and Co. (Manufacturers of Veegum) in their publication "Veegum—The Versatile Ingredient for Pharmaceutical Formulations" at p 19 describe a tablet formulation in which Veegum is added after granulation (tablet No. 2). There is no reference in the publication to a formulation of a tablet in which Veegum is added during granulation.

In contrast to the above recommendations, we have found that a swellable clay such as Veegummust be added during granulation to meet the British Pharmacopoeia (B. P.) standard for dispersible tablets (presently set at a dispersion time of 3 minutes or less). If the swellable clay is added only after granulation the dispersion time is too high to meet the above standard.

By using Veegum and other swellable clays in the manner described above, we have been able to prepare water-dispersible tablets containing a variety of therapeutically active compounds. The resulting tablets can readily be dispersed in water to form a dispersion which can be drunk by a patient.

According to the present invention there is provided a water-dispersible tablet comprising a therapeutically active compound selected from the group consisting of an analgesic propionic acid derivative, a tranquillising benzodiazepine, an anti-viral nucleoside derivative (for example acyclovir), an anti-protozoal napthoquinone, allopurtnol, oxopurinol, anti-convulsant 1,2,4 triazine derivative (for example lamotrigine) and trimethoprim (optionally in combination with sulphamethoxazole), together with an effective amount of a pharmaceutically acceptable swellable clay to provide a tablet which is capable of dispersing in water within a period of 3 minutes to provide a dispersion which is capable of passing through a sieve screen with a mesh aperture of 710 μm in accordance with the test for dispersible tablets defined in the British Pharmacopoeia, 1988, Volume II, page 895.

The above-defined therapeutically active compound employed in the tablet according to the invention is hereinafter referred to as "the active compound".

The present invention further provides a process for the preparation of a water-dispersible tablet comprising a therapeutically active compound selected from the group consisting of an analgesic propionic acid derivative, a tranquillising benzodiazepine, an anti-viral nucleoside derivative, an anti-protozoal napthoquinone, allopurinol, oxopurinol, anti-convulsant 1,2,4 triazine derivative and trimethoprim (optionally in combination with sulphamethoxazole), together with an effective amount of a pharmaceutically acceptable swellable clay which comprises bringing the said active compound into association with the said swellable clay to provide a water-dispersible tablet which is capable of dispersing in water within a period of 3 minutes to provide a dispersion which is capable of passing through a sieve screen with a mesh aperture of 710 μm in accordance with the test for dispersible tablets defined in the British Pharmacopoeia, 1988, Volume II, page 895. A particularly preferred active compound is lamotrigine.

Preferably said process comprises the steps of:
a) admixing in dry, finely-divided form the active compound with an effective amount of a pharmaceutically acceptable swellable clay, optionally with the addition of one or more other pharmaceutical carriers or excipients;
b) addition of a quantity of a pharmaceutically acceptable liquid sufficient to moisten the dry mixture;
c) granulation of the resulting moist mixture to form granules;
d) drying the granules and optionally blending the granules with other optional carriers or excipients such as lubricants, glidants, flavouring agents and disintegrating agents; and
e) compression of the granules to form a tablet which is capable of dispersing in water within a period of 3 minutes to provide a dispersion which is capable of passing through a sieve screen with a mesh aperture of 710 μm in accordance with the above defined British Pharmacopoeia test for dispersible tablets.

"The apparatus and method in accordance with the test for dispersible tablets in the British Pharmacopoeia, 1988, Volume II, page 895, Appendix XII; is as follows with the apparatus comprising
(i) a rigid basket-rack assembly supporting six cylindrical glass tubes 75.0 to 80.0 mm long, 21.5 mm in internal diameter and with a wall thickness of about 2 mm;
(ii) a cylindrical disc for each tube, each 20.55 to 20.85 mm in diameter and 9.35 to 9.65 mm thick, made of transparent plastic with a relative density of 1.18 to 1.20, pierced with five holes, each 2 mm in diameter, one in the centre and the other four spaces equally on a circle of radius 6 mm from the center of the disc, there being four equally spaced grooves cut in the lateral surface of the disc in such a way that at the upper surface of the disc they are 9.5 mm wide and 2.55 mm deep and at the lower surface 1.6 mm square;
(iii) two superimposed transparent plastic plates 90 mm in diameter and 6 mm thick, perforated by six holes having the same diameter as the tubes and holding the tubes vertically, the holes being equidistant from the centre of the plate and equally spaced from the another, and a piece of woven gauze made from stainless steel wire 0.635 mm in diameter and having nominal mesh apertures of 2.00 mm attached to the underside of the lower plate;
(iv) said plates being held rigidly in position and 77.5 mm apart by vertical metal rods at the periphery and a metal rod fixed to the center of the upper plate to enable the assembly to be attached to a mechanical device capable of raising and lowering it smoothly through a distance of 50 to 60 mm at a constant frequency of between 28 and 32 cycles per minute,
(v) said assembly being suspended in water at 19° to 21° C. held in a 1000-ml beaker, the volume of water being such that when the assembly is in the highest position the wire mesh is at least 15 mm below the surface of the water and when the assembly is in the lowest position the wire mesh is at least 25 mm above the bottom of the beaker and the upper open ends of the tubes remain above the surface of the water, said method consisting of introducing one tablet into each of the six tubes, suspending said assembly in the beaker containing the water and operating the apparatus of a maximum period of three minutes so that all six of the tablets disperse".

A tablet according to the invention, as well as being quickly dispersible in water, has the added advantage that it meets the British Pharmacopoeia (B. P.) test for dispersible tablets in respect of dispersion times and dispersion quality (i.e. passage through a 710 μm sieve).

Preferably the dispersion time of a tablet according to the invention is less than 2 minutes, more preferably less than 1.50 minutes and most preferably less than 1 minute.

A further advantage of the tablets according to invention is that because a relatively fine dispersion is formed the tablet will have a lower dissolution time and thus the drug may be absorbed into the blood stream much faster. Furthermore the fast dispersion times and relatively fine dispersions obtained with tablets according to the invention are also advantageous for swallowable tablets. Thus tablets according to the invention can be presented both for dispersion in water and also for directly swallowing. Those tablets according to the invention that are intended for swallowing are preferably film-coated to aid swallowing. Such film-coating however increases the dispersion time up to 5 minutes determined in accordance with the above-mentioned B. P. test.

According to a further feature of the present invention therefore we provide a water-dispersible film-coated tablet comprising a therapeutically active compound selected from the group consisting of an analgesic propionic acid derivative, a tranquillising benzodiazepine, an antiviral nucleoside derivative, an anti-protozoal napthoquinone, allopurinol, oxopurinol, an anti-convulsant 1,2,4-triazine derivative and trimethoprim (optionally in combination with sulphamethoxazole), together with an effective amount of a pharmaceutically acceptable swellable clay to provide a film-coated tablet which is capable of dispersing in water within a period of 5 minutes to provide a dispersion which is capable of passing through a sieve screen with a mesh aperture of 710 μm in accordance with the above-defined British Pharmacopoeia test for dispersible tablets subject to the variation of the said period specified in the test from 3 minutes to 5 minutes. The references herein to tablets according to the invention include both film-coated and non-film-coated tablets.

After the dispersion has passed through the 710 μm mesh screen, there should be substantially no residue, except fragments of undissolved tablet coating or shell, remaining on the screen or adhering to the lower surface of the disc, if a disc optionally has been used; and if any residue remains, it should consist of a soft mass having no palpably firm, unmoistened core.

The particle size distribution of the dispersion particularly when the active compound is acyclovir are set out in the following table with the increasingly preferred values being quoted from left to right.

| Particle Size (μm)* | BP Standard | Preferably | More Preferably | Most Preferably |
|---|---|---|---|---|
| <710 | <100% | 100% | 100% | 100% |
| <300 | — | >50% | >70% | >80% |
| <200 | — | — | >50% | >70% |
| <150 | — | — | — | >50% |

*(equivalent spherical volume diameter)

Examples of active compounds which have been employed in the tablets according to the invention are listed below together with respective patent publications, (in appropriate instances) which teach how to make them and infections or medical conditions which can be treated by them (incorporated by reference): acyclovir (UK No.1523865), lamotrigine (EP Nos. 021 121 and 247 829), diazepam, paracetamol, (both commercially available), 1-(β-D-arabinofuranosyl)-5-propy-1-ynyl-uracil (EP No. 0272 065), 2-[4-(4-chlorophenyl)cyclohexyl]-3-hydroxy-1,4-naphthoquinone (EP No. 0123 238), allopurinol (G. B. No. 1445 983).

Examples of other active compounds include: 3'-azido-3'-deoxythymidine (EP No. 0196 185), 5-prop-1-ynyl-1-(5-trimethylacetyl-β-D-arabinofuranosyl)uracil (EP No. 0375 164), 2-(2-amino-1,6-dihydro-6-oxo-9H(purin-9-yl)methoxy)ethyl-valinate (EP No. 0308 065), 2',3'-dideoxy-5-ethynyl-3'-fluorouridine (EP No. 0356 166), 5-chloro-1-(2,3-dideoxy-3-fluoro-β-erythropentofuranosyl)uracil (EP No. 0305 117 and EP No. 0317 128), penciclovir, i.e. 9-[4-hydroxy-3-(hydroxymethyl)butyl]guanine (EP No. 141927), famciclovir, i.e. 2-amino-9-[4-acetoxy-3-(acetoxymethyl)butyl] purine (EP No. 0182024) and E-5-(2-bromovinyl)-1-β-arabinofuranosyluracil (EP No. 0031 128), dextromethorphan, pseudophedrine, acrivastine, triprolidine, guaiphenesine, dihydrocodeine, codeine phosphate and ascorbic acid.

Preferably the active compound is lamotrigine, i.e. (3,5-diamino-6-(2,3-dichlorophenyl)-1,2,4-triazine, more preferably acyclovir or pharmaceutically acceptable salts of these compounds which have acceptable dispersibility in water. Thus, for example, a suitable salt of lamotrigine is the isethionate salt (i.e. 2-hydroxymethanesulphonate).

It will be appreciated that reference to any active compound also includes any pharmaceutically acceptable salts thereof.

The term "swellable clay" as used herein includes layered clays (such as smectites), porous fibrous clay minerals, and synthetic clay materials related in structure to layered clays and porous fibrous clays.

The term "layered clays" as used herein includes substantially homogeneous layered clays and mixtures thereof, and interstratified or mixed layered clays. Substantially homogeneous layered clays includes the smectite group for example dioctahedral and trioctahedral types. Examples of dioctahedral smectites are the montmorillonite group (montmorillonoids); magnesium and other (e.g. calcium) aluminium silicates such as Veegum in its various grades e.g. Veegum, Veegum HV, Veegum F, and Veegum WG); almasilate; fullers earth (e.g. Surrey finest); American fullers earth; bentonire; beidellite; cheto montmorillonite, Wyoming montmorillonite, Utah montmorillonite; Tatalia and Chambers montmorillonites; and iron rich smectites such as nontrite (e.g. Garfield nontronite) and ferrian smectites.

Examples of triocatahedral smectites (also known as saponites) are Swinefordite, hectorire, stevensite. Examples of smectites containing more unusual elements are Volkhonsite, Medmontite, Sauconite, nickel smectites and vanadium smectites. As well as the montmorillonite group, related smectites such as vermiculites may also have application.

The term "interstratified or mixed layer clays", as used herein includes clays involving different layers arranged in a regular or irregular structure. The most common examples of such clays have generally two components in substantially equal proportions and have been given mineral names such as rectorite (mica-smectite), hydrobiotite (biotite-vermiculite), corrensiten (chlorite-smectite) allettite (talc-saponite). More irregular arrangements include illite-smectite, chlorite-smectite, and kaolinite-smectite. Further examples of interstratified clays are tosudite, tarasovite, allevardite, Japanese bentonite ("acid clays"), AWAZU acid clay, and kaolinite-smectite. Other mixed layer clays may include one or more of the following minerals: clinchlore, chamosite, nimite, thuringite, sudoite, and cookeite. Mixed layer smectities are also known e.g. interdispersed montmorillonite and beidellite layers. The layers of mixed layer clays may be homogeneous or non-homogeneous.

The term "porous fibrous clays" includes palygorskite and sepiolite such as, for example attapulgite and American fuller's earth.

The term "synthetic clay materials" as used herein includes materials related in structure to layered clays and porous fibrous clays such as synthetic hectorire (lithium magnesium sodium silicate) for example laponite$^R$.

It will be appreciated that within the scope of the invention the following classes of clays have application alone or in combination and in mixed layer clays: kaolinires, serpentines, pyrophyllites, talc, micas and brittle micas, chlorites, smectites and vermiculites, palygorskites and sepiolites. Other phyllosilicates (clay minerals) which may be employed in the tablets according to the invention are allophane and imogolite.

The following references describe the characterisation of clays of the above types: Chemistry of Clay and Clay Minerals. Edited by A. C. D. Newman. Mineralogical Society Monograph No. 6, 1987, Chapter 1; S. W. Bailey; Summary of recommendations of AIPEA Nomenclature Committee, Clay Minerals 15, 85–93; and A Handbook of Determinative Methods in Mineralogy, 1987, Chapter 1 by P. L. Hall.

Suitably the swellable clay is a pharmaceutically acceptable crystalline mineral clay having a lattice structure which expands upon hydration, preferably a pharmaceutically acceptable smectite or attapulgite clay, especially a montmorillonoid, more preferably yet a montmorillonoid chosen from the group consisting of montmorillonite, sauconite, vermiculite, bentonire and hectorire, still more preferably an aluminium magnesium silicate and most preferably Veegum$^R$.

The term "smectine" as used herein in relation to tablets of the present invention includes the smectites as exemplified herein and with reference to O'Brian P. and Williamson C. J., in "Clays and Clay Minerals vol. 38 No. 3 pp322–326, 1990" and the other clay nomenclature references set out hereinbefore.

The term "magnesium aluminium silicate" as used herein in relation to tablets of the present invention should be understood to include the Aluminium Magnesium Silicate defined in the *British Pharmacopoeia*, volume 1, pages 27–28, 1988 and the Magnesium Aluminium Silicate defined in the *United States Pharmacopoeia, National Formulary XVI*, pages 1943–1944, 1990. Advantageously, said silicate is in the form of a microfine powder having a No. 325 US Standard mesh particle size, a viscosity of 250 cps (±25%) for a 5.5% (w/v) aqueous dispersion and an acid demand (the volume in ml. of 0.1N hydrochloric acid required to reduce the pH of one gram to 4) of 618: such a material is available as VEEGUM F (R. T. Vanderbilt Co., New York, N.Y., U.S.A.; K & K-Greeff Chemicals Ltd., Croydon, Surrey CR9 3QL, England).

The amount of swellable clay employed in the tablet according to the invention generally depends on the weight of the tablet. Experiments with acyclovir indicate for a 100 mg tablet, amounts as low as 0.25% w/w of tablet can be used whereas for tablets of about 1000 mg to 1200 mg up to 60% w/w, advantageously up to 50% w/w preferably up to 40% w/w could be used to give a satisfactory dispersible tablet in accordance with the invention. Other practical considerations such as poor flow and compression properties may, however, limit the maximum percentage weight of clay which can be incorporated within any given weight of tablet. In our experiments up to 40% w/w of swellable clay was used for a tablet having a total weight of 1100 mg and gave fine dispersions and fast dispersion times.

Thus for a dispersible tablet containing an active compound defined hereinbefore such as acyclovir or lamotrigine, the intra-granular amount of swellable clay such as a crystalline mineral clay for example, magnesium aluminium silicate is suitably present in the following general ranges 0.25 to 60% w/w, preferably 0.25 to 50% w/w, more preferably 0.5 to 50% w/w, more preferably still 1 to 50% w/w, more preferably still 1 to 40% w/w, more preferably still 2 to 20% w/w, more preferably still 2.5 to 20% w/w, still more preferably 3 to 10% w/w, and most preferably 5 to 10%, most desirably about 5% w/w.

The tablets according to the invention will generally contain a pre-determined amount of the active compound, depending on the identity of the compound, the desired dosage and the total weight of the tablet.

When the active compound is acyclovir, the tablets generally contain 100 to 1000 mg, preferably 200 to 800 mg, such as 400 to 800 mg of the compound. Such dosage units may be administered one or more times, for example up to five times, per day, at the discretion of the physician, according to the age and condition of the patient and the particular condition being treated. For an acyclovir tablet having a total weight about 1000 to 1200 mg and containing about 750 to 850 mg of acyclovir, the swellable clay e.g. Veegum F, is preferably present in an amount of 40 to 120 mg intragranularly.

When the active compound is lamotrigine or a pharmaceutically acceptable salt thereof the tablets according to the invention conveniently contain 2.5 to 500 mg. desirably 5 to 250 mg. of lamotrigine calculated as lamotrigine base. Preferred said unit doses include 5 mg., 12.5 mg., 25 mg., 50 mg., 100 mg., 150 mg., 200 mg. and 250 mg., calculated as the base. For tablets having a total weight of about 55 to 65 mg and containing about 5 mg lamotrigine, the swellable clay, e.g. Veegum F, is preferably present in an amount of 2 to 4 mg, especially about 3 mg. Similarly for a tablet having a weight of about 220 to 350 mg and containing about 80 to 120 mg, preferably 100 mg of lamotrigine, the swellable clay, e.g. Veegum F, is preferably present in amount of 5 to 20 mg, especially about 12 mg.

In general the tablets according to the invention contain the active compound in the following percentage proportions:

Acyclovir—20 to 904 w/w, preferably 45 to 854 w/w
Lamotrigine—3 to 904 w/w, preferably 5 to 404 w/w
1-(β-D-arabinofuranosyl)-5-propynyl-1-ynyluracil 10 to 904 w/w, preferably 65 to 804 w/w
Paracetamol—50 to 904 w/w, preferably 60 to 754 w/w
2-[4-(4-chlorophenyl)cyclohexyl]-3-hydroxy-1,4-naphthoquinone—50 to 85% w/w, preferably 60 to 75% w/w
Allopurinol—25 to 804 w/w, preferably 45 to 654 w/w
Diazepam—4 to 304 w/w, preferably 8 to 164 w/w
Pseudoephedrine—5 to 50% w/w, preferably 15 to 30% w/w
Dextromethorphan—2 to 20% w/w, preferably 5 to 15% w/w
Triprolidine—10 to 50% w/w, preferably 20 to 30% w/w
Codeine phosphate
Dihydrocodeine
Ascorbic Acid
Acrivastine—1 to 10% w/w, preferably 2 to 5% w/w
Guaiphenesine—10 to 40% w/w, preferably 15 to 30% w/w
Ibuprofen—20 to 90% w/w, preferably 65 to 85% w/w When the active compound (such as acyclovir) is present in an amount of at least 60% w/w in tablets according to the invention, we have suprisingly found that the dispersion time remains substantially constant over a range of tablet hardnesses. This is a considerable quality control advantage since in industrial manufacture it is essential to maintain a constant tablet hardness. Tablets according to the invention can thus be produced with sufficient hardness and friability so that they can easily be film-coated. A tablet according to the invention should desirably have a friability of about 2% or less, preferably 0.5% or less.

Based on experiments that we have carried out, it has been found that in addition to the amount of swellable clay present within the granules of the tablet, a further amount of swellable clay may be present outside the granules. At very low intra-granular amounts (such as 1% w/w or below), higher extra-granular amounts (such as about 10% w/w or more) may decrease the dispersion time, but in general extra-granular addition has little or no effect on the dispersion time. The maximum percentage(s) of the clay present within the granules and, optionally outside the granules, may be limited by other practical considerations such as poor flow and compression properties.

Other excipients suitable for inclusion in the tablets according to the invention include the following:

a) Binders and Adhesives: we have found e.g. with acyclovir tablet formulations that if there is sufficient amount of swellable clay such as Veegum F present within the granules, then a separate binder is not required (i.e. the clay also acts as a binder). Preferably however a separate binder is present in a sufficient amount to provide a tablet having a satisfactory tablet hardness and satisfactory dispersion characterstics. The amount of binder will vary depending on the overall tablet formulation and type of binder used but general functional limits for most tablets of the invention are 0 to 25% w/w. The following binders and amounts are suitable for inclusion in a tablet according to the invention. The concentration of the binder in the granulation fluid (% w/v) is given (% w/w in tablet will vary according to the volume of granulating solution used to form a satisfactory tablet): Examples of binders are: acacia mucilage 0 to 25% w/v, preferably 1 to 5% w/v, alginic acid 0 to 20.0% w/v, preferably 1 to 5% w/v, polyvinylpyrrolidone (povidone) 0 to 15.0% w/v, preferably 0.5 to 5% w/v, gelatin 0 to 20.0% w/v, preferably 1 to 5.0% w/v, sucrose 0 to 70.0% w/v, preferably 2.0 to 20.0% w/v, starch mucilage 0 to 10.0% w/v, preferably 0.5 to 5.0% w/v, pregelatinised starch 0 to 10.0% w/v, preferably 0.5 to 5.0% w/v, starch paste 0 to 10.0% w/v, preferably 5.0 to 10.0% w/v, sodium alginate 0 to 5.0% w/v, preferably 1.0 to 3.0% w/v, sorbitol 0 to 10.0% w/v, preferably 3.0 to 10.0% w/v, tragacanth 0 to 20% w/v, preferably 5.0 to 10.0% w/v, glucose 0 to 50%, preferably 5 to 25% w/v, hydroxypropylmethyl cellulose (HPMC) 0 to 10% w/v, preferably 1.0 to 5.0% w/v, magnesium aluminium silicate 0 to 40% w/v, preferably 2 to 10% w/v, starch paste 0 to 25% w/v, preferably 5 to 15% w/v, polyvinylpyrrolidone 0 to 15% w/v, preferably 3 to 10% w/v, carboxymethylcellulose sodium 0 to 10% w/v, preferably 1 to 6% w/v, dextrin 0 to 50% w/v, preferably 5 to 25% w/v, ethyl cellulose 0 to 10% w/v, preferably 1 to 6% w/v, polyethylene glycol 0 to 5% w/v, guar gum 0 to 10% w/v, preferably. 1 to 5% w/v, zein 0 to 30% w/v, preferably 1 to 10% w/v, hydroxyethyl cellulose 0 to 5% w/v, preferably 2 to 4% w/v, hydroxypropyl cellulose up to 5% w/v, preferably 2 to 4% w/v, methyl cellulose up to 20% w/v, preferably 1 to 10% w/v, polymethacrylates up to 25% w/v, preferably 5 to 10% w/v, carboxymethylcellulose calcium 0 to 20% w/v, preferably 5 to 10% w/v.

b) Disintegrating agents: Tablets according to the invention can be formulated in the absence of separate disintegrating agents although their inclusion may be advantageous for their disintegration in water as an adjunct to the dispersion afforded by the clay above. Examples of suitable disintegrating agents which can optionally be incorporated into a tablet according to the invention are: microcrystalline cellulose (e.g. Avicel R) 0 to 30% w/w, preferably 5 to 10% w/w, Sodium carboxymethyl cellulose (e.g. Nymcel R) 0 to 5% w/w, preferably 1 to 2% w/w, calcium carboxymethyl cellulose 0 to 20% w/w, preferably 1 to 5% w/w, modified cellulose gum (e.g. Ac-Di-Sol R) 0 to 10% w/w, preferably 1 to 5% w/w, cross-linked povidone 0 to 10% w/w, preferably 2 to 6% w/w, alginic acid and alginates 0 to 10% w/w, 2 to 5% w/w, pregelatinised starch 0 to 10% w/w, preferably 0.5 to 5% w/w, sodium starch glycollate (e.g. Explotab R, Primojel R) 0 to 10% w/w, preferably 0.5 to 5% w/w, modified corn starch (e.g. starch 1500 R) 0 to 20% w/w, preferably 1 to 10% w/w, starch (e.g. potato/maize starch ) 0 to 15% w/w, preferably 0.2 to 10% w/w, ion exchange resin such as polacrin potassium (e.g. Amberlite IRP-88) up to 5% w/w, preferably 0.5 to 2.0% w/w.

Work with lamotrigine and other active compounds is supportive of the view that if LHPC is used a suitable dispersion can be obtained without the need for a separate wetting agent/surfactant.

c) Fillers: These serve the purpose of bulking up the tablet to a suitable size and aiding compressibility especially in lower dosage tablets. The amount of filler depends on its type, size of tablet and amount of active compound. When the concentration of active compound is below 60% w/w, more preferably 45% w/w and most preferably below 30% w/w, an inorganic water-insoluble filler is advantageously used. Examples of water-soluble fillers (which can be used in general quantities of 0 to 95% w/w) are: soluble lactose, compressible sugar, confectioners sugar, dextrose, mannitol, sodium chloride, sorbitol, xylitol, sodium chloride F. Examples of water-insoluble fillers (which can be used in general quantities of 0 to 93% w/w) are: calcium carbonate, magnesium carbonate, calcium phosphate (e.g. di and tri basic calcium phosphate), calcium sulphate, kaolin, microcrystalline cellulose, powdered cellulose, pregelatinized starch 5 to 75%, starch, barium sulphate, magnesium trisilicate, aluminium hydroxide.

Inclusion of a filler having a negative heat of solution in water, for example mannitol, sorbitol and xylitol, provides tablets which, in addition to being water-dispersible, are especially suitable for chewing in the mouth, the dissolving of such an excipient in the saliva producing a cool, pleasant sensation.

d) Lubricants: Generally lubricants are used in as low an amount as possible. Examples of lubricants with percentage weights which are suitable for a tablet are: stearates (e.g. magnesium or calcium stearate) 0.2 to 5% w/w, preferably 0.25 to 1% w/w, talc 0.19 to 5% w/w, preferably 1 to 2% w/w, polyethylene glycol 0.19 to 5% w/w, preferably 2 to 5% w/w, liquid paraffin 0.18 to 5% w/w, preferably 2 to 5% w/w, sodium lauryl sulphate 0.19 to 5% w/w, preferably 0.5 to 2% w/w, magnesium lauryl sulphate 0.12 to 5% w/w, preferably 1 to 2% w/w, colloidal silicon dioxide 0.1 to 5% w/w, preferably 0.1 to 1.0% w/w, palmitostearate 0.01 to 5% w/w, preferably 1 to 3% w/w, stearic acid 0.01 to 5% w/w, preferably 1 to 3% w/w, zinc stearate 0.01 to 2% w/w, 0.5 to 1.5% w/w, hydrogenated vegetable oil 0.5 to 5% w/w, preferably 1 to 3% w/w. More suitably the lower value is 0.25%.

e) Wetting agents/surfactants: examples with suitable amounts are: sodium dodecyl sulphate 0 to 10% w/w, preferably 0.5 to 2% w/w, sodium lauryl sulphate 0 to 10% w/w, preferably 0.1 to 3.0% w/w, polyoxyethylene sorbitan fatty acid esters (Tweens) 0 to 3% w/w, preferably 0.05 to 1.0% w/w, polyoxyethylene stearates 0 to 2% w/w, preferably 0.05 to 1.0% w/w, sorbitan fatty acid esters (Spans) 0 to 3% w/w, preferably 0.05 to 1.0% w/w.

f) Glidants: for example, talc 0 to 5% w/w, preferably 1 to 2% w/w, starch 0 to 15% w/w, preferably 2 to 10% w/w, magnesium stearate up to 5%, preferably 0–2.0% w/w, silica derivatives generally 0 to 1% w/w, preferably 0.2 to 0.5% w/w, such as colloidal silica (e.g. Aerosil) 0 to 0–5% w/w, preferably 0.25 to 3% w/w, pyrogenic silica 0 to 2% w/w, preferably 0.25 to 1% w/w, hydrated sodium silicoaluminate 0 to 2% w/w, preferably 0.5 to 1% w/w, colloidal silicon dioxide 0 to 0.5% w/w.

g) Flavouring agents: are used in for example approximate quantities of 0 to 5% w/w, preferably 0.25 to 2% w/w, orange, cherry and strawberry, raspberry, grape and passion fruit.

h) Sweetening agents: for example sodium saccharin 0 to 10% w/w, preferably, 0.5 to 5.0% w/w, aspartame 0 to 10% w/w, preferably 0.25 to 5.0% w/w, confectioners sugar 0 to 30% w/w, preferably 5 to 20% w/w, sorbitol 25 to 90% w/w, preferably 0.5 to 10% w/w, sucrose 0 to 85% w/w, preferably 0.5 to 20% w/w, xylitol 0–20% w/w, preferably 0.5 to 10% w/w.

Such materials may be incorporated at the appropriate stage(s) of the manufacturing process together with any other agents (e.g. colourants).

Based on the teachings and principles set out herein, the following general formulations are illustrative of tablets of the invention, and the skilled man given these teachings and principles will be able to make specific tablet formulations in accordance with the invention.

| INGREDIENT | CONCENTRATION (% w/w) in Tablet |
|---|---|
| Active compound | 5 to 90 |
| Swellable clay | 0.25 to 60 (preferably 0.25 to 50) |
| Binder | 0 to 25 |
| Disintegrating agent | 0 to 20 |
| Water-soluble filler | 0 to 95 |
| Water-insoluble filler | 0 to 95 |
| Wetting agent | 0 to 5 |
| Lubricant | 0.1 to 5 |
| Colours, flavours, sweeteners | 0 to 10 |
| Approximate Tablet weight: | 50–2000 mg |

Other aspects of the tablet preparation will now be discussed.

Suitably the dry mixing is effected with a mixing time of 5 minutes to 25 minutes preferably about 10 minutes.

The swellable clay can be dry mixed with the active compound and other excipients and then granulating solution added, or the clay and other excipients can be dispersed firstly in the granulating solution and then added to the active compound and any other excipients prior to granulation.

The liquid employed to moisten the dry mixture, prior to the granulation step, is preferably aqueous, for example water or a mixture of water and a suitable alcohol such as ethanol or isopropanol.

Wet mixing or granulating times which are suitable (depending on the type of mixer used) are 5 to 20 minutes.

Suitable granule drying times and conditions (which will vary according to the type of equipment used and batch size of granules) are about 50° to 80° C., (using a dryer such as with a tray or fluid bed dryer) to obtain a moisture content generally below about 4%.

Generally suitable compression weights and final table hardness will vary according to the size of tablet, but generally suitable values are as follows;

| Approximate Tablet weight (mg) | Approximate Tablet diameter (mm) | Approximate Target tablet hardness (Kp) |
|---|---|---|
| 60 | 5.6 | 1–2 |
| 80 | 6.4 | 3–4 |
| 125 | 7.4 | 4–5 |
| 250 | 8.6 | 5–6 |
| 330 | 9.4 | 6–8 |
| 500 | 11.0 | 10–12 |
| 600 | 11.8 | 10–14 |
| 1000 | 14.0 | 12–16 |

The tablets may optionally be film-coated, for example with hydroxypropylmethyl cellulose, polyethylene glycol or titanium dioxide, and/or may be scored and/or may be polished, for example with polyethylene glycol 8000. If the tablets are film-coated, this makes them easier to swallow or chew (i.e. the tablets are suitable for either dispersion in water or for direct swallowing or chewing), but the dispersion time is increased.

The present invention also provides:

a) Granules containing an active compound and a pharmaceutically acceptable swellable clay, suitable for use in the preparation of a water-dispersible tablet according to the invention.

b) Use of granules as defined above in the preparation of a water-dispersible tablet according to the invention. Optionally, a further amount of swellable clay may be added after granulation and before compression;

c) Use of a pharmaceutically acceptable swellable clay as a dispersing agent in the preparation of a water-dispersible tablet containing an active compound (as defined above);

d) Use in human medicinal therapy of a water-dispersible tablet comprising an active compound (as defined above), together with an effective amount of pharmaceutically acceptable swellable clay within the granules of the tablet.

Suitably the swellable clay of the invention is a pharmaceutically acceptable crystalline mineral compound, such as aluminium magnesium silicate (e.g. Veegum).

The therapeutic use of a tablet of the invention includes both treatment and prophylaxis.

The invention has been found to have particular application with lamotrigine because of the long term instability of lamotrigine in aqueous media. Furthermore dispersible tablets containing lamotrigine have been found to give a finer dispersion than tablets using more common disintegrating agents such as Explotab.

Further aspects of the invention illustrated with respect to lamotrigine are:

e) Granules, suitable for use in the preparation of a water-dispersible compressed tablet, comprising lamotrigine or a pharmaceutically acceptable salt thereof together with a pharmaceutically acceptable crystalline mineral clay as dispersing agent;

f) Use of granules as defined above in the preparation of a water-dispersible compressed tablet which may involve the addition of a further amount of crystalline mineral clay compound after granulation and before compression; and g) Use of a pharmaceutically acceptable crystalline mineral clay as dispersing agent in the preparation of a water-dispersible compressed tablet containing lamotrigine or a pharmaceutically acceptable salt thereof.

h) A water-dispersible tablet comprising lamotrigine or a pharmaceutically acceptable salt thereof together with a pharmaceutically acceptable crystalline mineral clay having a lattice structure which expands upon hydration as dispersing agent. The lamotrigine or a pharmaceutically acceptable salt thereof together with the mineral clay are comprised within the tablet in granulated form.

i) A method for the preparation of a lamotrigine water-dispersible tablet which comprises the steps of admixture in dry, finely-divided form of lamotrigine or a pharmaceutically acceptable salt thereof and the pharmaceutically acceptable crystalline mineral clay which may be chosen from the group consisting of attapulgite, smectite and montmorillonoid clays or magnesium aluminium silicate, optional addition of other pharmaceutical ingredients such as fillers (eg lactose, avicel or mannitol), disintegrants, binders, etc.

addition of a quantity of a pharmaceutically acceptable liquid sufficient to moisten the mixture, granulation of the resulting moist mass, drying of the granules and blending of the granules with optional lubricants, glidant, flavours, disintegrants etc., and formation of the blend into a tablet.

j) Use in human medicine of a water-dispersible compressed tablet comprising lamotrigine or a pharmaceutically acceptable salt thereof together with a pharmaceutically acceptable crystalline mineral clay as dispersing agent, and k) A method for the treatment in a human being of a disorder of the central nervous system which comprises administration of a water-dispersible compressed tablet comprising lamotrigine or a pharmaceutically acceptable salt thereof together with a pharmaceutically acceptable crystalline mineral clay as dispersing agent.

Especially preferred tablets are those wherein the lamotrigine is present as the base.

The said tablets may be employed in human medicine in the treatment of disorders of the central nervous system and in particular in the treatment of epileptic seizures. They may be administered one or more times per day, for example up to five times per day, at the discretion of the attendant physician and dependent upon the age and condition of the patient, the particular disorder being treated, the unit dose adopted and the total dose required. A suitable daily dose for the treatment of epileptic seizures will generally lie in the range of 5 to 500 mg., more often in the range of 25 to 400 mg., calculated as the base.

The physical size of the said tablets is desirably such as to permit their dispersion, prior to oral ingestion, in an acceptably small volume of water. Thus, for example, a tablet containing 5 mg. (calculated as the base) of lamotrigine or a salt thereof, a dose especially suitable for paediatric use, is advantageously small enough to disperse in the volume of water held in a standard 5 ml. medicine spoon.

Tablets of the invention containing lamotrigine (or a salt thereof) advantageously include a magnesium aluminium silicate such as Veegum F as the swellable clay together with further optional pharmaceutical carriers or excipients referred to above such as binders, lubricants, fillers, disintegrating agents etc.

In such tablets the ingredients are advantageously present in the following proportions: lamotrigine: 2% w/w to 90% w/w preferably 5% w/w to 40% w/w; swellable clay: 0.25% w/w to 40% w/w preferably 0.25% w/w to 10% w/w.

A suitable formulation of a dispersible tablet containing 25 to 200 mg lamotrigine would be:

| | |
|---|---|
| Lamotrigine | 30% w/w to 50% w/w, preferably 35–45% |
| Calcium carbonate | 26% w/w to 46% w/w, preferably 31–41% |
| LHPC-LH11 or microcrystalline cellulose (e.g. Avicel PH101) | 5% w/w to 30% w/w, preferably 5–15% |
| Magnesium aluminium silicate Veegum F or bentonite | 0.25% w/w to 30% w/w, preferably 0.25–10% |
| Povidone or pre-gelled starch | 0.25% w/w to 5.0% w/w, preferably 0.5–2% <br> 1.0% w/w to 8.0% w/w, preferably 2–5% |
| Sodium starch glycollate | 0% w/w to 8% w/w, preferably 0–5% |
| Magnesium stearate | 0.25% w/w to 2% w/w, preferably 0.25–1% |
| and if optionally film coated: | |
| Opadry | 0.1% w/w to 2% w/w, preferably 0.25–1% |
| Polyethylene glycol 8000 | 0.1% w/w to 0.5% w/w, preferably 0.1–0.2% |

A suitable formulation of a dispersible tablet containing 5 mg to 50 mg of lamotrigine would be as follows, (values being in % w/w).

| | |
|---|---|
| Lamotrigine | 3–13 preferably 5–11 |
| Lactose or calcium carbonate | 50–60 preferably 53–59 |
| Microcrystalline cellulose (e.g. Avicel PH101) or LHPC-LH11 | 20–35 preferably 24–30 |
| Sodium starch glycollate | 0–8 preferably 0–5 |
| Magnesium aluminium silicate Veegum F or bentonite | 0.25–30 preferably 0.25–10 |
| Povidone K30 or pregelled starch | 0.25–5.0 preferably 0.5–2.0 <br> 1.0–8.0 preferably 2–5 |
| Sodium docusate | 0–0.5 preferably 0.5–0.15 |
| Sodium saccharine | 0–3 preferably 0.5–2 |
| Magnesium stearate | 0.25–2 preferably 0.25–1 |
| and if optionally film coated | |
| Opadry | 0.1–2.0 preferably 0.25–1 |
| Polyethylene glycol 8000 | 0.1–0.5 preferably 0.1–0.2 |

As referred to above, the present invention is particularly applicable to the formulation of water-dispersible tablets containing acyclovir as the active compound.

Acyclovir is a compound which has been found to have potent activity against viruses of the herpes family, particularly herpes simplex and herpes varicella zoster. Such activity has been demonstrated by the outstanding success of acyclovir in the therapeutic treatment of clinical conditions such as genital herpes caused by the herpes varicella zoster virus.

In the treatment of certain conditions, it may be necessary to administer acyclovir to the patient in relatively large dosages to achieve the effective therapeutic levels of drug in the plasma, particularly when oral administration is desired. For example, in the treatment of shingles, it is recommended to administer acyclovir at a dosage regime of 800 mg five times per day. A tablet formulation containing 800 mg of acyclovir is currently available but its relatively large size sometimes renders it difficult to swallow by elderly patients, such patients being particularly susceptible to shingles. This problem is obviated by the water-dispersible tablets according to the invention which enable relatively high doses of acyclovir to be administered in a drinkable dispersion by the oral route.

The advantageous water-dispersibility of tablets according to the invention containing acyclovir as the active compound is especially surprising in view of the poor water-dispersibility demonstrated by tablets containing conventional disintegrating agents such as sodium starch glycollate, cross-linked povidone and cross-linked sodium carboxymethylcellulose.

Yet further aspects of the invention with respect to acyclovir are as follows:

l) A granulate comprising acyclovir together with a pharmaceutically acceptable magnesium aluminium silicate compound;

m) Use of a granulate according to e) above for the manufacture of a water-dispersible tablet formulation.

n) Use of magnesium aluminium silicate in the manufacture of a water-dispersible tablet formulation of acyclovir.

o) A water-dispersible pharmaceutical tablet formulation comprising acyclovir together with a pharmaceutically acceptable magnesium aluminium silicate compound.

p) A process for the preparation of a pharmaceutical tablet formulation which comprises admixing acyclovir with a magnesium aluminium silicate compound and optionally one or more further pharmaceutical carriers or excipients, granulating the resulting mixture with a pharmaceutically acceptable liquid, drying the resulting granulate, optionally mixing the dried granulate with one or more further pharmaceutical carriers or excipients, and subsequently compressing the dried granulate to form tablets. The liquid employed in the above granulation step is advantageously aqueous, for example, an aqueous ethanol mixture. The resulting tablets may be subsequently film coated for example with hydroxypropylmethyl cellulose, titanium dioxide or polyethylene glycol and, if desired, polished for example with polyethylene glycol 8000.

Tablets according to the invention containing acyclovir advantageously include a magnesium aluminium silicate such as Veegum F as the swellable clay optionally together with further pharmaceutical carriers or excipients referred to above such as disintegrating agents, binders, fillers, lubricants etc.

In such tablets the ingredients are advantageously present in the following proportions: acyclovir 40 to 98% w/w, preferably 75 to 85% w/w, swellable clay 0.5 to 40% w/w, preferably 0.5 to 10% w/w.

A suitable formulation of an acyclovir dispersible tablet containing from 200 mg–800 mg acyclovir would be:

| | |
|---|---|
| Acyclovir | 70% w/w to 90% w/w, preferably 75–85% w/w |
| Povidone or pregelled starch | 0.25% w/w to 5% w/w, preferably 0.5–2% w/w |
| Magnesium aluminium silicate Veegum F or bentonite | 0.5% w/w to 30% w/w, preferably 0.5–10% w/w |

| | | |
|---|---|---|
| Microcrystalline cellulose Avicel PH101 or LHPC-LH11 | 5% w/w to 25% w/w, preferably 5–15% w/w | |
| Sodium starch glycollate | 0% w/w to 8% w/w, preferably 0–5% w/w | |
| Magnesium stearate | 0.25% w/w to 2% w/w, preferably 0.25–1.0% w/w | |
| and if optionally film coated: | | |
| Opadry | 0.1% w/w to 2% w/w, preferably 0.25–1.0% w/w | |
| Polyethylene glycol 8000 | 0.1% w/w to 0.5% w/w, preferably 0.1–0.2% w/w | |

The following Examples illustrate the present invention. Examples 1 to 6 and 29 are comparative examples while examples 7–28, 30 and 31 describe the preparation of tablets according to the invention in which the active compound is acyclovir.

In accordance with the invention, to illustrate that the disintegration time remains substantially constant at different tablet hardnesses, the formulation of Example 7 was compressed at approximately 8 kp (7a), 12 kp (7b) and 18 kp (7c) and the results noted hereafter.

| Example Number | 1 mg/tablet | 2 mg/tablet | 3 mg/tablet | 4 mg/tablet |
|---|---|---|---|---|
| Intra-granular: | | | | |
| Acyclovir* | 848.0 | 848.0 | 844.0 | 844.0 |
| Avicel PH101 | 60.0 | NIL | 101 | NIL |
| Lactose | 120.0 | NIL | NIL | NIL |
| Starch (maize) | NIL | NIL | 50 | NIL |
| Explotab | NIL | 75.0 | 50 | NIL |
| Primogel | NIL | NIL | NIL | 75.0 |
| Ac-Di-Sol | 83.0 | NIL | 23 | NIL |
| Kollidon CL starch | NIL | NIL | NIL | NIL |
| Saccharin sodium | 20.0 | 10.0 | NIL | NIL |
| Sodium lauryl sulphate | 5.0 | NIL | 3.0 | NIL |
| Sodium docusate | NIL | 1.0 | NIL | 0.5 |
| Dicalc.phosph.dihyr. | NIL | NIL | NIL | 200.0 |
| Povidone K30 | NIL | 10.0 | 22 | 11.2 |
| Extra-granular: | | | | |
| Ac-Di-Sol | 40.0 | NIL | NIL | NIL |
| Avicel PH102 | 60.0 | 94 | NIL | NIL |
| Amberlite IRP88 | NIL | NIL | NIL | 50.0 |
| Kollidon CL | NIL | NIL | 60.1 | NIL |
| Mg stearate | 12.0 | 10.0 | 10.1 | 11.0 |
| Tablet weight (mg) | 1248.0 | 1048.0 | 1163.2 | 1191.7 |

| Example Number | 5 mg/tablet | 6 mg/tablet | 7 mg/tablet | 8 mg/tablet | 9 mg/tablet |
|---|---|---|---|---|---|
| Acyclovir | 844.0 | 848.0 | 844.0 | 848.0 | 848.0 |
| Avicel PH 101 | 101.0 | 83.46 | 100.0 | 89.0 | 89.0 |
| Veegum F | NIL | NIL | 53.0 | 53.0 | 53.0 |
| Sodium starch glycollate (Explotab) | 90.0 | 39.37 | 42.0 | 42.0 | 42.0 |
| Povidone K30 | 11.0 | 10.27 | NIL | 11.0 | 11.0 |
| Magnesium stearate | 9.5 | 8.85 | 9.4 | 9.4 | 9.4 |
| Film coat composite 1: Opadry | NIL | NIL | NIL | NIL | 7.86 |
| Film coat composite 2: Polyethylene glycol 8000 | NIL | NIL | NIL | NIL | 2.097 |
| Tablet weight (mg) | 1055.5 | 989.95 | 1048.4 | 1052.4 | 1062.4 |

*In the following examples except examples 13, 14 and 15, the actual quantity of acyclovir used is calculated from a factor so as to provide 800 mg of acyclovir per tablet. (The factor for acyclovir is typically 105.5 equivalent to 100 acyclovir). In examples 13, 14 and 15, the actual quantity of acyclovir used was adjusted from the factor so as to provide 800 mg of acyclovir per tablet.

| Example Number | 10 mg/tablet | 11 mg/tablet | 12 mg/tablet |
|---|---|---|---|
| Acyclovir | 848.0 | 848.0 | 848.00 |
| Avicel PH 101 | 118.5 | 71.1 | 86.8 |
| Veegum F | 26.5* | 53.0 | 53.0 |
| Primojel | 42.0 | 42.0 | 42.0 |
| Povidone K30 | NIL | 20.9 | 5.2 |
| Magnesium stearate | 9.4 | 9.4 | 9.4 |
| Tablet weight (mg) | 1044.4 | 1044.4 | 1044.4 |

*Veegum added as a paste - example contains no PVP-K30 as a binder.

Examples of Acyclovir formulations

| Example Number | 13 mg/tablet | 14 mg/tablet | 15 mg/tablet |
|---|---|---|---|
| Component (mg/tablet) | | | |
| Acyclovir | 800.0 | 800.0 | 800.0 |
| Avicel PH 101 | 100.0 | 89.0 | 89.0 |
| Veegum F | 53.0 | 53.0 | 110.0 |
| Sodium starch glycollate | 42.0 | 42.0 | 42.0 |
| Povidone K30 | NIL | 11.0 | 11.0 |
| Magnesium stearate | 9.4 | 9.4 | 9.9 |
| Tablet weight (mg) | 1004.4 | 1004.4 | 1061.9 |

| Example Number | 16 % w/w | 16 mg/tablet | 17 % w/w | 17 mg/tablet | 18 % w/w | 18 mg/tablet | 19 % w/w | 19 mg/tablet |
|---|---|---|---|---|---|---|---|---|
| Acyclovir | 79.95 | 848.0 | 75.54 | 795.00 | 65.47 | 689.00 | 55.00 | 583.00 |
| Avicel PH101 | 8.86 | 89.0 | 8.86 | 89.00 | 8.86 | 89.00 | 8.86 | 89.00 |
| Veegum F | 5.28 | 53.0 | 10.00 | 106.00 | 20.00 | 212.00 | 30.00 | 318.00 |
| Explotab | 4.18 | 42.0 | 4.18 | 42.00 | 4.18 | 42.00 | 4.18 | 42.00 |
| Povidone K30 | 1.09 | 11.0 | 1.09 | 11.00 | 1.09 | 11.00 | 1.09 | 11.00 |
| Magnesium stearate | 0.94 | 9.4 | 0.94 | 9.40 | 0.94 | 9.40 | 0.94 | 9.40 |
| Tablet weight (mg) | 100.0 | 1052.4 | 100.0 | 1052.4 | 100.0 | 1052.4 | 100.0 | 1052.4 |

| Example Number | % w/w | 20 mg/tablet | % w/w | 21 mg/tablet | % w/w | 22 mg/tablet |
|---|---|---|---|---|---|---|
| Acyclovir | 45.32 | 477.00 | 84.3 | 890.00 | 44.93 | 848.00 |
| Avicel PH101 | 8.86 | 89.00 | 8.86 | 89.00 | 8.86 | 157.76 |
| Veegum F | 40.00 | 424.00 | 1.00 | 10.60 | 40.00 | 712.22 |
| Explotab | 4.18 | 42.00 | 4.18 | 42.00 | 4.18 | 74.43 |
| Povidone K30 | 1.09 | 11.00 | 1.09 | 11.00 | 1.09 | 19.41 |
| Magnesium stearate | 0.94 | 9.40 | 0.94 | 9.40 | 0.94 | 16.74 |
| Tablet weight (mg) | 100.00 | 1052.4 | 100.00 | 1052.4 | 100.00 | 1828.56 |

| Example Number | % w/w | 23 mg/tablet | % w/w | 24 mg/tablet | % w/w | 25 mg/tablet | % w/w | 26 mg/tablet |
|---|---|---|---|---|---|---|---|---|
| Acyclovir | 65.47 | 689.00 | 55.00 | 583.00 | 45.32 | 477.00 | 79.65 | 848.00 |
| Avicel PH101 | 8.86 | 89.00 | 8.86 | 89.00 | 8.86 | 89.00 | 8.86 | 89.0 |
| Veegum F | *20.00 | (106.00 (106.00 | *30.00 | (159.00 (159.00 | *40.00 | (212.00 (212.00 | 5.28 | 53.0 |
| Explotab | 4.18 | 42.00 | 4.18 | 42.00 | 4.18 | 42.00 | 4.18 | 42.0 |
| Povidone K30 | 1.09 | 11.00 | 1.09 | 11.00 | 1.09 | 11.00 | 1.09 | 11.0 |
| Magnesium stearate | 0.94 | 9.40 | 0.94 | 9.40 | 0.94 | 9.40 | 0.94 | 9.4 |
| Tablet weight (mg) | 100.00 | 1052.4 | 100.00 | 1052.4 | 100.00 | 1052.4 | 100.00 | 1052.4 |

*In these examples the Veegum is distributed equally both intra-granularly and extra-granularly.

| Example Number | 27 % w/w | 27 mg/tablet | 28 % w/w | 28 mg/tablet | 29 % w/w | 29 mg/tablet | 30 mg/tablet | 31 mg/tablet |
|---|---|---|---|---|---|---|---|---|
| Acyclovir | 84.43 | 848.00 | 84.68 | 848.00 | 84.93 | 848.00 | 848.0 | 840.0 |
| Avicel PH101 | 8.86 | 83.95 | 8.86 | 83.70 | 8.86 | 83.46 | 89.0 | 89.0 |
| Veegum F | 0.50 | 4.74 | 0.25 | 2.36 | 0.00 | 0.00 | — | — |
| Bentonite | — | — | — | — | — | — | 53.0 | NIL |
| Attapulgite | — | — | — | — | — | — | NIL | 53.0 |
| Explotab | 4.18 | 39.60 | 4.18 | 39.49 | 4.18 | 39.37 | 42.0 | 42.0 |
| Povidone K30 | 1.09 | 10.32 | 1.09 | 10.30 | 1.09 | 10.27 | 11.0 | 11.0 |
| Magnesium stearate | 0.94 | 8.91 | 0.94 | 8.88 | 0.94 | 8.85 | 9.1 | 9.1 |
| Tablet weight (mg) | 100.00 | 995.53 | 100.00 | 992.73 | 100.00 | 989.95 | 1052.1 | 1044.1 |

Examples 32–40 describe the preparation of tablets according to the invention in which the active compound is lamotrigine.

| Example Number | 32 mg/tablet | 33 mg/tablet | 34 mg/tablet | 35 mg/tablet | 36 mg/tablet | 37 mg/tablet | 38 mg/tablet | 39 | 40 |
|---|---|---|---|---|---|---|---|---|---|
| Lamotrigine | 100 | 5.0 | 5.0 | 100 | 100 | 100 | 100 | 100.0 | 100.0 |
| Calcium carbonate | 95 | NIL | NIL | NIL | 95 | NIL | NIL | 95.0 | 90.0 |
| Lactose | NIL | 34 | 35.0 | 15 | NIL | 98.1 | 84 | | |
| L HPC-LH11 | 25 | NIL | NIL | NIL | 25 | NIL | NIL | 25.0 | 25.0 |
| Veegum F | 12 | 3.0 | 3.0 | 7.5 | 12.0 | 16.0 | 12 | 12.0 | 12.0 |
| Povidone K30 | 3.0 | 0.6 | 0.6 | 1.5 | 3.0 | 3.2 | 3 | 3.0 | 3.0 |
| Explotab | 10.0 | 2.0 | 1.2 | 6.0 | NIL | 12.8 | 10.0 | — | 10.0 |
| Sodium Saccharin | 2.5 | 0.5 | 0.5 | NIL | NIL | NIL | NIL | — | — |
| Aspartame | NIL | NIL | NIL | 4.0 | 7.5 | NIL | 7.5 | 7.5 | 7.5 |
| Microcrystalline cellulose (Avicel PH101) | NIL | 17 | 17 | 15 | NIL | 89.6 | 23 | — | — |
| Sodium docusate | NIL | 0.05 | NIL | NIL | NIL | 0.26 | 0.2 | — | — |
| Magnesium stearate | 2.5 | 0.4 | 0.4 | 1.5 | 2.5 | 3.2 | 2.5 | 2.5 | 2.5 |
| Flavour | | | | | | | | — | 1.24 |
| Tablet weight (mg) | 250 | 62.55 | 62.70 | 150.5 | 245 | 323.16 | 242.2 | 245.0 | 251.24 |

Examples of Tablet Formulations containing other Active Compounds

| Example Number | 41 | 42 | 43 | 44 | 45 |
|---|---|---|---|---|---|
| Active compound* (mg) | 200.0 | 300.0 | 758.0 | 500.0 | 5.0 |
| Avicel PH101 | 50.0 | 64.0 | 83.0 | — | 17.0 |
| Explotab | 12.3 | 21.0 | 40.0 | 27.0 | 2.5 |
| L-HPC-LH11 | 50.0 | — | 41.0 | 87.0 | — |
| Lactose | — | 110.0 | — | — | 34.0 |
| Veegum F | 16.7 | 27.0 | 50.0 | 71.0 | 3.0 |
| Citric acid monohydrate | — | — | 0.8 | — | — |
| Na docusate | — | — | 0.8 | — | — |
| Saccharin sodium | — | — | 0.5 | — | — |
| Povidone K30 | 3.3 | 10.8 | 20.0 | 20.0 | 0.7 |
| Magnesium Stearate | 1.0 | 2.7 | 5.0 | 2.0 | 0.4 |
| Flavour (Pineapple) | — | — | 2.0 | — | — |
| Tablet Weight (mg) | 333.3 | 535.5 | 1001.1 | 707.0 | 62.6 |

* The active compound for each Example is as follows:-
Example 41 - 1-(β-D-arabinofuranosyl)-5-propynyluracil
Example 42 - Allopurinol
Example 43 - 2-[4-(4-chlorophenyl)cyclohexyl]-3-hydroxy-1,4,napthoquinone
Example 44 - Paracetamol
Example 45 - Diazepam

Method of Preparation

The tablets described in Examples 1–45 above were prepared according to the following general method: p0 (a) A dry mixture was made of all components except Povidone/PVP K30, sodium docusate (if present) and magnesium stearate;

(b) The Povidone/PVP K30 and sodium docusate (if present) were dissolved in 50% aqueous alcohol to form a granulation solution;

(c) The granulation solution was added to the dry mixture to form granules;

(d) The wet granules were dried in a fluid bed dryer;

(e) The granules were then sifted through a 1000 μm diameter mesh sieve; and (f) The dried granules were blended with the magnesium stearate and compressed to form tablets.

Flavouring agents where present were added at blending step (f) above.

This general method is illustrated with respect to the following specific examples.

Example 8: Uncoated Tablets (a) A dry mixture was made of all components except Povidone/FVP K30 and magnesium stearate using a Diosna P100 (high shear mixer—granulator) for 3 minutes.

(b) The Povidone/PVP K30 was dissolved in 50% aqueous alcohol to form a granulation solution.

(c) The granulation solution was added to an approximate quantity of 300 ml per kg dry weight to the dry mixture to form granules. Wet mixing was carried out for approximately 5 minutes.

(d) The wet granules were dried in an Aeromatic T3 fluid bed drier at a temperature of 70° C. for approximately 30 minutes. The moisture content of the granules was approximately 4%.

(e) The granules were then sifted through a 1000 μm diameter mesh sieve using a Jackson Crockatt No.7 sifter.

(f) The dried granules were blended with the magnesium stearate using a collette mixer for approximately 10 minutes and compressed to form tablets using a Manesty D3 Rotary tablet press fitted with caplet shaped punches of approximately 19.3 mm length and 9.0 mm breadth. Tablets were compressed to a weight of 1052 mg±2%.

This granule can be used to make other strengths of acyclovir dispersible tablets, e.g. 200 mg and 400 mg, compressing the dried granules to a weight of respectively 263 mg and 526 mg, using round punches with diameters of respectively 8.6 mm and 11.0 mm.

Example 9: Film Coated Tablets

Steps (a) to (f) described in Example 8 were repeated to form an uncoated tablet which was then film-coated by the following procedure.

The film-coating apparatus used was a Manesty Accellacota 10. The coating suspension was sprayed onto the tablet cores to a target weight increase of between 0.5–1.0% using suitable parameters of:
pan rotation speed (8.5 rpm)
spray (application rate (~20 g per min)
inlet temperature (~75° C.)
exhaust temperature (~53° C.).

A polish coat of PEG8000 was then applied to the film-coated tablets, to a further weight gain of 0.1–0.2%.

Examples 13 to 15

In Example 13, Acyclovir, Avicel PH101, Sodium starch glycollate and Veegum F are dry mixed in a mixer. The mixture is then granulated after adding a sufficient volume of 50% aqueous alcohol (IMS). The resulting granules are dried, blended with the magnesium stearate and then compressed to form tablets.

Example 14

The procedure described in Example 13 for the preparation of the granules and formation of the tablets is employed except that granulation of the dry mixture is effected with the Povidone in a 50% aqueous alcohol solution. Film coating of the resulting tablets can be optionally effected by treating the tablets with a dispersion of Opadry white dispersion in purified water and drying the coated tablets which are subsequently polished with a solution of polyethylene glycol 8000, USNF in 50% aqueous alcohol (IMS).

For Example 15, the procedure described in Example 13 for the preparation of the granules and formation of the tablets is employed except that granulation of the dry mixture was effected with the Povidone in a 50% aqueous alcohol solution.

Example 33

(a) A dry mixture was made of all components except Povidone/PVP K30 and magnesium stearate using a Z-blade Morton Mixer, mixing for 10 minutes at a slow speed.

(b) The Povidone/PVP K30 was dissolved in 50% aqueous alcohol to form a granulation solution;

(c) The granulation solution was added to an approximate quantity of 350 ml per kg dry weight to the dry mixture to form granules;

(d) Wet mixing was carried out for approximately 10 minutes. The wet granules were sieved through a 2000 μm mesh sieve;

(e) The wet granules were dried in an Aeromatic fluid bed drier at a temperature of 70° C. for approximately 25 minutes;

(f) The granules were then sifted through a 1000 μm diameter mesh sieve;

(g) The dried granules were blended with the magnesium stearate using a Rotomixer rotary blender for 5 minutes and compressed to form tablets using a Manesty D3 Rotary press fitted with 5.6 mm diameter round (normal curvature) punches and dies. Tablets were compressed to a weight of 62.55 mg±2%.

Flavouring agents may be added at blending step (g) above.

For a 50 mg tablet, the same procedure was used, except that a die of 11.8 mm diameter was used and the tablets were compressed to a weight of 625.5 mg±2%.

The lamotrigine tablets could be optionally film coated using the same procedure as described for Example 9.

The tablets prepared in accordance with the above Examples were then tested as follows.

Tablet Evaluation Methods

1. Average tablet weight

Twenty tablets were weighed on an analytical balance and the average tablet weight calculated.

2. Tablet breaking strength (kilo pond-kD)

5 tablets were individually tested using a Schleuniger crushing strength tester, and the average breaking strength calculated.

3. Friability (% loss)

10 tablets, accurately weighed, were subjected to 10 minutes friability testing using a Roche Friabilator. The tablets were dedusted, reweighed, and the weight loss due to the friability was calculated as a percentage of the initial weight.

4. Dispersion Disintegration time DT (BP 1988)

6 tablets were tested in accordance to the above-defined BP test (without discs) for dispersible tablets. This utilises water at a temperature of 19°–21° C.

5. Dispersion Quality

In accordance with the BP uniformity of dispersion test for dispersible tablets (BP 1988 Volume II page 895), two tablets were placed in 100ml of water at 19°–21° C. and allowed to disperse. A smooth dispersion was produced which passed through a 710 μm mesh sieve.

Granule Evaluation Methods

1. Loss on Drying (LOD)

The residual moisture content of the granule (LOD) was determined on a 3–4g sample using a Computrac moisture analyser set to 90° C. operated in accordance with the manufacturer's procedure.

2. Weight Median Diameter (WMD)

A 10 g sample of granule was sifted for 2 minutes at suitable pulse and sift amplitudes in an Allen Bradley sonic sifter in accordance with manufacturer's instructions. Sieves of 710 μm, 500 μm, 355 μm, 250 μm, 150 μm, 106 μm and 53 μm were used. The WMD was calculated from the cumulative percentage undersize size distribution using a computer programme.

| Example Number | Actual Average Tablet Weight (mg) | Target Tablet Weight (mg) | Average Thickness (mm) | Average Breaking Strength (Kp) | Friability (%) | Disintegration time** First Tablet | Disintegration time** Last Tablet | Loss on Drying (% LOD) | Weight median diameter WMD (μm) | Tablet shape/ maximum diameter |
|---|---|---|---|---|---|---|---|---|---|---|
| \multicolumn{11}{c}{Acyclovir Granule and Tablet Evaluation Results} |
| 1 | — | 1248.0 | — | 11.0 | — | | 12'17" | 1.43 | — | Caplet* |
| 2 | — | 1048.0 | — | 11.6 | — | | 7'26" | 1.59 | — | Caplet |
| 3 | 1176 | 1163.2 | — | 10.7 | — | >10' | — | 2.28 | — | Round 14.0 mm |
| 4 | — | 1191.7 | — | 13.7 | — | | 4'50" | 1.18 | — | Round 14.0 mm |
| 5 | 1053 | 1055.5 | — | 15.0 | — | | 4'21" | 1.75 | 186 | Round 14.0 mm |
| 6 | 983 | 989.95 | 5.46 | 10.8 | 0.34 | 6'27" | 7'26" | 1.43 | 315 | Caplet |
| 7a | 1022 | 1048.4 | — | 7.2 | 2.74 | | 0'33" | 1.31 | 233 | Caplet |
| 7b | 1046 | 1048.4 | — | 12.8 | 0.47 | | 0'42" | 1.31 | 233 | Caplet |
| 7c | 1048 | 1048.4 | — | 17.1 | 0.19 | | 0'44" | 1.31 | 233 | Caplet |
| 8 (uncoated) | 1049 | 1052.4 | 7.0 | 14.6 | 0.18 | | 0'35" | 4.06 | 138 | Caplet |
| 9 (coated) | 1053 | 1062.4 | 6.99 | 16.1 | negligible | | 1'05" | 4.06 | 138 | Caplet |
| 10 | — | 1044.4 | — | 14.4 | 0.11 | — | 0'32" | 2.65 | 123 | Caplet |
| 11 | — | 1044.4 | — | 15.3 | 0.24 | — | 0'46" | 1.46 | 196 | Caplet |
| 12 | — | 1044.4 | — | 13.3 | 0.73 | — | 0'27" | 1.76 | 105 | Caplet |
| 13,14,15*** | | | | | | | | | | |
| 16 | 1051.24 | 1052.4 | 7.1 | 11.6 | 0.49 | 0'46" | 0'49" | 1.12 | 185 | Caplet |
| 17 | 1059.54 | 1052.4 | 7.0 | 11.8 | 0.46 | 0'28" | 0'30" | 2.18 | 125 | Caplet |
| 18 | 1060.79 | 1052.4 | 6.90 | 11.5 | 0.62 | 0'17" | 0'19" | 1.46 | 178 | Caplet |
| 19 | 1053.4 | 1052.4 | 6.70 | 11.6 | 0.71 | 0'19" | 0'24" | 2.00 | 73 | Caplet |
| 20 | 1057.6 | 1052.4 | 6.71 | 9.1 | 2.45 | 0'20" | 0'23" | 1.81 | 90 | Caplet |
| 21 | 1048.8 | 1052.4 | 7.24 | 11.5 | 0.85 | 2'18" | 2'59" | 1.15 | 341 | Caplet |
| 22 | 1743.9 | 1828.56 | 10.40 | 11.6 | 2.19 | 0'29" | 0'31" | 1.84 | 83 | Caplet |
| 23 | 1054.2 | 1052.4 | 6.90 | 11.5 | 0.09 | 0'43" | 0'51" | 1.84 | 157 | Caplet |
| \multicolumn{11}{l}{**All dispersions passed through a 710 μm sieve (BP uniformity of dispersion test).} |
| 24 | 1059.1 | 1052.4 | 6.90 | 11.4 | 0.02 | 0'55" | 1'00" | 0.68 | 142 | Caplet |
| 25 | 1052.6 | 1052.4 | 6.70 | 11.9 | 0.09 | 1'30" | 1'42" | 1.59 | 118 | Caplet |
| 26a)# | 130.6 | 131.55 | 2.80 | 4.2 | 0.56 | 0'25" | 0'28" | 1.34 | 296 | 7.4 mm Round |
| 26b)# | 526.0 | 526.2 | 4.81 | 12.84 | 0.79 | 0'26" | 0'30" | 1.34 | 296 | 11.0 mm Round |
| 26c)# | 1216.5 | 1215.0 | 8.20 | 11.10 | 0.83 | 0'45" | 0'51" | 1.34 | 296 | Caplet |
| 27 | 125.7 | 124.4 | 3.68 | 3.68 | 0.71 | 0'33" | 0'39" | 1.21 | 334 | 7.4 mm Round |
| 28 | 124.7 | 124.1 | 2.78 | 3.55 | 0.65 | 0'44" | 0'47" | 1.90 | 332 | 7.4 mm Round |
| 29 | 982.9 | 989.95 | 5.46 | 10.8 | 0.34 | 6'27" | 7'26" | 1.43 | 315 | Caplet |

| | | | | | | | | | | |
|---|---|---|---|---|---|---|---|---|---|---|
| 30 | 1041.2 | 1052.1 | — | 11.8 | — | 1'30" | 1'55" | 1.62 | 227 | Caplet |
| 31 | 1038.6 | 1044.1 | — | 16.6 | 1.59 | 1'50" | 2'10" | 1.96 | 150 | Caplet |

*Approximate dimensions of caplet were: 19.3 mm long, 9.0 mm wide, 7.0 mm thick.
**Disintegration times measured in accordance with BP test for dispersible tablets. All dispersions passed through a 710 μm sieve (BP uniformity of dispersion test).
Same granule formulation, but different compression weights giving approximately: a = 100 mg, b = 400 mg and c = 925 mg of acyclovir per tablet.
***Examples 13, 14 and 15 disintegrated in 0'30" to 1'30".

Lamotrigine Granule and Tablet Evaluation Results

| | | | | | | | | | | |
|---|---|---|---|---|---|---|---|---|---|---|
| 32 | 251.0 | 250.0 | — | 4.8 | 1.32 | — | 0'24" | 2.28 | 74 | 8.6 round |
| 33a)## | 62.06 | 62.55 | 2.30 | 1.5 | 0.9 | — | 0'09" | 1.90 | 98 | 5.6 round |
| 33b) | 630.0 | 625.5 | 5.40 | 9.6 | 0.71 | — | 0'33" | 1.90 | 98 | 11.8 round |
| 34 | 61.95 | 62.70 | 2.27 | 1.3 | 1.3 | — | 0'06" | 1.96 | 102 | 5.6 round |
| 35 | 150.2 | 150.5 | 3.32 | 4.5 | 1.01 | 0'23" | 0'26" | 3.9 | 168 | 7.4 round |
| 36 | 245.7 | 245.0 | — | 4.9 | 1.44 | — | 0'20" | 3.0 | — | 8.6 round |
| 38 | 237.5 | 242.2 | 3.79 | 5.2 | 1.42 | 0'30" | 0'36" | 3.1 | 182 | 8.6 round |
| 40a)+ | 62.4 | 62.8 | — | 1.5 | 1.10 | — | 0'19" | 1.4 | — | 5.6 round |
| 40b)+ | 248.7 | 251.24 | — | 4.5 | 1.45 | — | 0'44" | 1.4 | — | 8.6 round |

+Tablets containing lamotrigine a) 25 mg and b) 100 mg made by varying the tablet compression weight.
Tablets containing a) 5 mg and b) 50 mg lamotrigine made by varying the tablet compression weight.

Granule and Tablet Evaluation Results for Other Actives

| | Actual | | | | | | Granule Properties | | |
|---|---|---|---|---|---|---|---|---|---|
| | Average Tablet | Target Tablet | Average Breaking | Fria- | Disintegration time** | | Loss on | Weight median | Tablet |
| Example Number | Weight (mg) | Weight (mg) | Strength (Kp) | bility (%) | First Tablet | Last Tablet | Drying (% LOD) | diameter WMD (μm) | shape size |
| 41 | — | 333.3 | 9.5 | 0.31 | 0'28" | 0'32" | 1.40 | 112 | 9.4 mm round |
| 42 | 536.7 | 535.5 | 9.0 | 0.87 | 0'45" | 0'50" | 1.00 | 246 | 11.0 mm round |
| 43 | 993.6 | 1001.1 | 17.0 | 1.26 | 0'50" | 1'05" | 1.87 | 167 | 14.0 mm round |
| 44 | 706.7 | 707.0 | 16.5 | 0.80 | 0'45" | 0'50" | 1.90 | 83 | 12.6 mm round |
| 45 | 63.3 | 62.6 | 2.6 | 0.79 | 0'05" | 0'07" | 2.06 | — | 5.6 mm round |

**All dispersions passed through a 710 μm sieve (BP uniformity of dispersion test).

A particle size analysis was carried out on the dispersion of a tablet of Example 9 in accordance with the following method.

The particle size distribution was determined using a Malvern 2600 particle analyser as follows. The instrument was set to analyse particles in liquid with magnetic stirrer fitted. A 300 mm focal length lens was used.
1. Disperse tablet in 100 ml of de-ionised water.
2. Agitate solution for approximately 2 hours.
3. Filter or centrifuge solution to obtain liquor which should be saturated with all ingredients present in the tablet.
4. Disperse second tablet in 50 ml of saturated liquor allowing 3 minutes to fully disperse. Agitate vigorously and remove a sample of the dispersion within 5 minutes adding sufficient quantity to the Malvern PIL cell containing the liquor to obtain an observation value of 0.15–0.30. Analyse sample.

The particle size distribution was as follows:
Particle size: (as equivalent spherical volume)
<710 μm—100%
<300 μm—98.7%
<200 μm—86.7%
<130 μm—50% (median particle size).

I claim:

1. A process for the preparation of a water-dispersible tablet having lamotrigine and comprising 3% to 90% w/w lamotrigine, 0.25 to 40% of a pharmaceutically acceptable swellable clay and an additional pharmaceutically acceptable disintegrating agent; said process comprising bringing lamotrigine into association with said swellable clay and additional disintegrating agent to form granules, and then compressing the granules to form a tablet which is capable of dispersing in water within a period of 3 minutes to provide a dispersion which is capable:

a) of dispersing in water to provide a dispersion which passes through a sieve screen with a mesh aperture of 710 μm;
b) of disintegrating within three minutes when examined by the following apparatus and method in accordance with the test for dispersible tablets of the British Pharmacopoeia, 1988, volume II, page 895; said apparatus consisting of:
(i) a rigid basket-rack assembly supporting six cylindrical glass tubes 75.0 to 80.0 mm long, 21.5 mm in internal diameter and with a wall thickness of about 2 mm;
(ii) a cylindrical disc for each tube, each 20.55 to 20.85 mm in diameter and 9.35 to 9.65 mm thick, made of transparent plastic with a relative density of 1.18 to 1.20, pierced with five holes, each 2 mm in diameter, one in the centre and the other four spaced equally on a circle of radius 6 mm from the center of the disc, there being four equally spaced grooves cut in the lateral surface of the disc in such a way that at the upper surface of the disc they are 9.5 mm wide and 2.55 mm deep and at the lower surface 1.6 mm square;
(iii) two superimposed transparent plastic plates 90 mm in diameter and 6 mm thick, perforated by six holes having the same diameter as the tubes and holding the tubes vertically, the holes being equidistant from the centre of the plate and equally spaced from one another, and a piece of woven gauze made from stainless steel wire 0.635 mm in diameter and having nominal mesh apertures of 2.00 mm attached to the underside of the lower plate;
(iv) said plates being held rigidly in position and 77.5 mm apart by vertical metal rods at the periphery and a metal rod fixed to the center of the upper plate to enable the assembly to be attached to a mechanical device capable of raising and lowering it smoothly through a distance of 50 to 60 mm at a constant frequency of between 28 and 32 cycles per minute;

(v) said assembly being suspended in water at 19° to 21° C. held in a 1000-ml beaker, the volume of water being such that when the assembly is in the highest position the wire mesh is at least 15 mm below the surface of the water and when the assembly is in the lowest position the wire mesh is at least 25 mm above the bottom of the beaker and the upper open ends of the tubes remain above the surface of the water;

said method consisting of introducing one tablet into each of the six tubes, suspending said assembly in the beaker containing the water and operating the apparatus for a maximum period of three minutes so that all six of the tablets disperse.

2. A process for the preparation of a water-dispersible tablet having lamotrigine, comprising the steps of:

(a) admixing in dry freely divided form 3% to 90% w/w lamotrigine, 0.25 to 40% w/w of a pharmaceutically acceptable swellable clay and an additional pharmaceutically acceptable disintegrating agent;

(b) addition of a quantity of pharmaceutically acceptable aqueous liquid sufficient to moisten the dry mixture;

(c) granulation of the resulting moist mixture to form granules;

(d) drying the granules and blending the granules with lubricant; and (e) compression of the granules to form a tablet to provide a tablet which is capable:

(f) of dispersing in water to provide a dispersion which passes through a sieve screen with a mesh aperture of 710 µM;

g) of disintegrating within three minutes when examined by the following apparatus and method in accordance with the test for dispersible tablets of the British Pharmacopoeia, 1988, volume II, page 895; said apparatus consisting of:

(i) a rigid basket-rack assembly supporting six cylindrical glass tubes 75.0 to 80.0 mm long, 21.5 mm in internal diameter and with a wall thickness of about 2 mm;

(ii) a cylindrical disc for each tube, each 20.55 to 20.85 mm in diameter and 9.35 to 9.65 mm thick, made of transparent plastic with a relative density of 1.18 to 1.20, pierced with five holes, each 2 mm in diameter, one in the center and the other four spaced equally on a circle of radius 6 mm from the center of the disc, there being four equally spaced grooves cut in the lateral surface of the disc in such a way that at the upper surface of the disc they are 9.5 mm wide and 2.55 mm deep and at the lower surface 1.6 mm square;

(iii) two superimposed transparent plastic plates 90 mm in diameter and 6 mm thick, perforated by six holes having the same diameter as the tubes and holding the tubes vertically, the holes being equidistant from the center of the plate and equally spaced from one another, and a piece of woven gauze made from stainless steel wire 0.635 mm in diameter and having nominal mesh apertures of 2.00 mm attached to the underside of the lower plate;

(iv) said plates being held rigidly in position and 77.5 mm apart by vertical metal rods at the periphery and a metal rod fixed to the center of the upper plate to enable the assembly to be attached to a mechanical device capable of raising and lowering it smoothly through a distance of 50 to 60 mm at a constant frequency of between 28 and 32 cycles per minute;

(v) said assembly being suspended in water at 19° to 21° C. held in a 1000-ml beaker, the volume of water being such that when the assembly is in the highest position the wire mesh is at least 15 mm below the surface of the water and when the assembly is in the lowest position the wire mesh is at least 25 mm above the bottom of the beaker and the upper open ends of the tubes remain above the surface of the water;

said method consisting of introducing one tablet into each of the six tubes, suspending said assembly in the beaker containing the water and operating the apparatus for a maximum period of three minutes so that all six of the tablets disperse.

3. A process as claimed in claim 2 wherein a filler is also admixed with lamotrigine, the swellable clay, and additional disintegrating agent.

4. A process as claimed in claim 2 wherein a binder is added to assist in forming the granules.

5. A process as claimed in claim 2 where the tablet is further film coated.

6. a process as claimed in claim 2 wherein the swellable clay is smectite or attapulgite.

7. A process as claimed in claim 6 wherein the smectite is selected from the group consisting of montmorillonite group.

8. A process as claimed in claim 7 wherein the montmorillonite is magnesium aluminium silicate or bentonite.

9. A process for the preparation of a water-dispersible tablet having lamotrigine, comprising the steps of:

(a) admixing in dry finely divided form 30% to 50% w/w lamotrigine, 26% to 46% w/w calcium carbonate, 0.25 to 10% w/w of a pharmaceutically acceptable swellable clay selected from the group consisting of magnesium aluminium silicate and bentonite, 0 to 8% w/w sodium starch glycolate, and an excipient selected from the group consisting of 5 to 30% w/w of low hydroxypropylcellulose and microcrystalline cellulose;

(b) addition of a quantity of pharmaceutically acceptable granulating solution with dissolved binder selected from the group consisting of 0.5% to 2% povidone and 2% to 5% pregelled starch;

(c) granulation of the resulting moist mixture to form granules;

(d) drying the granules and blending the granules with 0.25% to 2% magnesium silicate; and (e) compression of the granules to form a tablet to provide a tablet which is capable:

f) of dispersing in water to provide a dispersion which passes through a sieve screen with a mesh aperture of 710 µM;

g) of disintegrating within three minutes when examined by the following apparatus and method in accordance with the test for dispersible tablets of the British Pharmacopoeia, 1988, volume II, page 895; said apparatus consisting of:

(i) a rigid basket-rack assembly supporting six cylindrical glass tubes 75.0 to 80.0 mm long, 21.5 mm in internal diameter and with a wall thickness of about 2 mm;

(ii) a cylindrical disc for each tube, each 20.55 to 20.85 mm in diameter and 9.35 to 9.65 mm thick, made of transparent plastic with a relative density of 1.18 to 1.20, pierced with five holes, each 2 mm in diameter, one in the center and the other four spaced equally on a circle of radius 6 mm from the center of the disc, there being four equally spaced grooves cut in the lateral surface of the disc in such a way that at the upper surface of the disc they are 9.5 mm wide and 2.55 mm deep and at the lower surface 1.6 mm square;

(iii) two superimposed transparent plastic plates 90 mm in diameter and 6 mm thick, perforated by six holes having the same diameter as the tubes and holding the tubes vertically, the holes being equidistant from the center of the plate and equally spaced from one another, and a piece of woven gauze made from stainless steel wire 0.635 mm in diameter and having nominal mesh apertures of 2.00 mm attached to the underside of the lower plate;

(iv) said plates being held rigidly in position and 77.5 mm apart by vertical metal rods at the periphery and a metal rod fixed to the center of the upper plate to enable the assembly to be attached to a mechanical device capable of raising and lowering it smoothly through a distance of 50 to 60 mm at a constant frequency of between 28 and 32 cycles per minute;

(v) said assembly being suspended in water at 19° to 21° C. held in a 1000-ml beaker, the volume of water being such that when the assembly is in the highest position the wire mesh is at least 15 mm below the surface of the water and when the assembly is in the lowest position the wire mesh is at least 25 mm above the bottom of the beaker and the upper open ends of the tubes remain above the surface of the water;

said method consisting of introducing one tablet into each of the six tubes, suspending said assembly in the beaker containing the water and operating the apparatus for a maximum period of three minutes so that all six of the tablets disperse.

* * * * *